United States Patent [19]

Marsh

[11] Patent Number: 5,647,502
[45] Date of Patent: Jul. 15, 1997

[54] WALL MOUNTED MEDICAL WASTE DISPOSAL CONTAINER WITH PIVOTED TOP CLOSURE LID

[75] Inventor: Gordon Marsh, West Hills, Calif.

[73] Assignee: Devon Industries, Inc., Chatsworth, Calif.

[21] Appl. No.: 527,874

[22] Filed: Sep. 14, 1995

Related U.S. Application Data

[63] Continuation of Ser. No. 62,187, May 17, 1993, Pat. No. 5,494,186.
[51] Int. Cl.⁶ .................................................. B65D 25/24
[52] U.S. Cl. .......................... 220/481; 220/254; 220/324; 220/335; 220/339; 220/908; 206/366
[58] Field of Search .................................... 220/263, 264, 220/324, 326, 337, 481, 374, 339, 254, 259, 335, 908, 910; 206/365, 366; 232/43.1, 43.2, 44, 47

[56] References Cited

U.S. PATENT DOCUMENTS

| | | |
|---|---|---|
| 3,306,486 | 2/1967 | Martino et al. . |
| 3,342,368 | 9/1967 | Matry . |
| 3,749,274 | 7/1973 | Mele et al. . |
| 4,095,712 | 6/1978 | Perrella . |
| 4,736,860 | 4/1988 | Bemis . |
| 4,776,478 | 10/1988 | Miller et al. . |
| 4,779,728 | 10/1988 | Hanifl et al. . |
| 4,874,103 | 10/1989 | Quisenberry et al. . |
| 4,955,501 | 9/1990 | Hodge . |
| 5,058,764 | 10/1991 | Gaba . |
| 5,080,251 | 1/1992 | Noack . |
| 5,152,420 | 10/1992 | Bird et al. . |

Primary Examiner—Stephen Cronin

[57] ABSTRACT

A terrestrial wall mounted medical waste disposal container having a flexibly pivoted top closure lid is shown. The container includes a lid mount which is fitted in a sealing manner upon the top of the container, and a flexible lid which is attached to the lid mount. The lid mount has a recessed top face which abuts and slopes toward an entrance aperture in the top face of the mount. The flexible lid is divided into two portions by a living hinge. The larger and outer portion of the lid is pivotable along the hinge. In the lid's extreme opened position it lies flat on the recessed top face of the lid mount and so also slopes toward the entrance aperture; in this maximally extended position the lid's outer edge comes sufficiently close to the wall that it is impossible to deposit a waste item accidentally behind the lid or the container. Also, the lid in any opened position not only constitutes a barrier against mis-deposition of waste items, but it also provides a sloping surface leading to the aperture and such that any item deposited upon it will tend gravitationally to fall into the aperture.

17 Claims, 4 Drawing Sheets

WALL MOUNTED MEDICAL WASTE DISPOSAL CONTAINER WITH PIVOTED TOP CLOSURE LID

This application is a continuation of U.S. application Ser. No. 08/062,187, filed May 17, 1993, now U.S. Pat. No. 5,494,186.

BACKGROUND OF THE INVENTION

1. Field of the Invention

The present invention relates to a wall mounted medical waste disposal container having a flexibly pivoted top closure lid and, more particularly, to a lid and lid mount which are adapted to greatly reduce the possibility of accidental deposit of waste items anywhere other than in the container's entrance aperture.

2. Brief Description of the Prior Art

Various types of containers for hospital use have been developed for receiving medical waste in a surgical operating room, pre-op or post-op room, or a patient's room. These containers are particularly designed to protect the user of such containers, such as doctors, nurses, or other hospital personnel, from the hospital waste products that may be disposed therein. Such hospital waste products might include surgical sharps, such as needles, syringes, scalpel blades, or the like, or might include gauzes, bandages, or sponges. It is important to prevent the user of a sharps container from being accidentally cut or punctured by its contents.

Examples of such containers include those shown in U.S. Pat. No. 5,058,764 entitled "Mounting Bracket Having A Hidden Lock For A Sharps Collection System" and U.S. Pat. No. 5,080,251, entitled "Tortuous Path In-Patient Room Medical Waste Disposal Container".

In addition to protecting the user of a sharps container from its contents and to being easily sealed and disposed of, a sharps collection and disposal system should be readily available within a patient's room, an operating room, or a pre-op or post-op room. This ready availability feature can be accomplished by providing a mounting bracket for mounting the sharps collection system at a convenient location near an operating area, or a bed location in a pre-op, post-op, or patient's room.

However, the sharps collection and disposal systems currently available in the industry could be improved to ensure that the person attempting to deposit a medical waste item into the container may not miss the container opening when his or her attention is momentarily distracted and he or she attempts to deposit the item into the container in an inattentive manner, such as looking in one direction and reaching for the top of the container with one hand out of the line of sight of the depositor's eyes.

Thus, one object of the present invention is to provide a relatively "foolproof" deposit-acceptance system in such a manner that if the depositor's grasp is relaxed anywhere over the top of the container the waste item will be directed by the combined force of gravity and prepared sloping shape of the top of the container to draw the waste item into the top aperture without fail.

Another object of the present invention is to prevent a situation from occurring where the waste item is deposited behind the lid and its presence there remains hidden until the time to close the lid.

A still further object of the invention is to prevent a potentially even more undesirable result in which the medical waste item is accidentally deposited behind the container and between the container and the wall upon which it is mounted, remaining concealed there until the container is dismounted from its wall attachment in order to be discarded.

SUMMARY OF THE INVENTION

In accomplishing the foregoing objects and other objects, there is provided a wall mounted medical waste disposal container having a flexibly pivoted top closure lid. The container includes a lid mount which is fitted in a sealing manner upon the top of the container, and a flexible lid which is attached to the lid mount. The lid mount has a recessed top face which abuts and slopes toward an entrance aperture in the top face of the mount. The flexible lid is divided into two portions by a living hinge. The larger and outer portion of the lid is pivot-able along the hinge and has two extreme positions. In the lid's extreme opened position it lies flat on the recessed top face of the lid mount. Therefore, like the recessed face, the lid in its maximally opened outward position also slopes toward the entrance aperture. When the lid is in this maximally extended position, flat upon the recessed top face, its outer edge comes sufficiently close to the wall upon which the container is mounted that it is impossible to deposit a waste item accidentally behind the lid and on the top of the lid mount or behind the container and between the container and the wall. In the preferred embodiment, the tension in the living hinge is so chosen that the natural equilibrium position of the lid is in this maximally extended position. However, the lid in any opened position not only constitutes a barrier against mis-deposition of waste items intended for deposition into the container through the aperture in the top of the lid mount, but it also provides a sloping surface which leads to the aperture and is such that any item deposited upon it will, by the force of gravity, tend to slide or roll into the aperture.

The smaller inner portion of the lid is permanently attached to the recessed top face of the lid mount by means of a conventional system of hooks and slots. Both the lid and the lid mount may be strengthened by inclusion in their fabrication of stiffening structural ribs. The lid mount may be permanently attached to the top of the container by conventional attachment means, such as a system of corresponding hooks and slots.

When the time has come to remove the container from the wall in order to dispose of both it and the medical waste items which it contains, the lid may be permanently locked into its closed position by means of another system of slots and hooks.

BRIEF DESCRIPTION OF THE DRAWINGS

Further advantages and objects of the present invention will be understood after careful consideration of the following specification and drawings, wherein.

DESCRIPTION OF THE PREFERRED EMBODIMENTS

Figure 1:
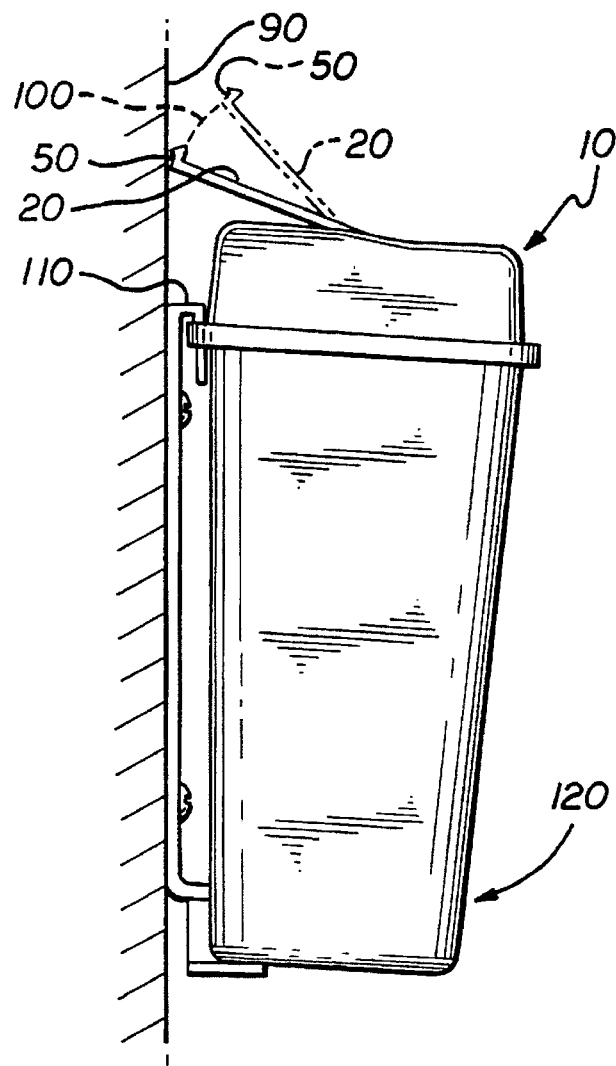
FIG. 1 is a side view of the container attached to a wall and showing the container lid mount on top of the container and the lid in an open position.

Referring now to the drawings, medical waste disposal container 120 is attached to wall 90 by wall attachment means 110. Fitted in a sealing manner to the top of container 120 is a container closure lid mount 10. As shown in FIGS. 2 through 6 the lid mount has a recessed top face 11 which slopes toward an entrance aperture located upon the top face of lid mount 10.

Figure 2:
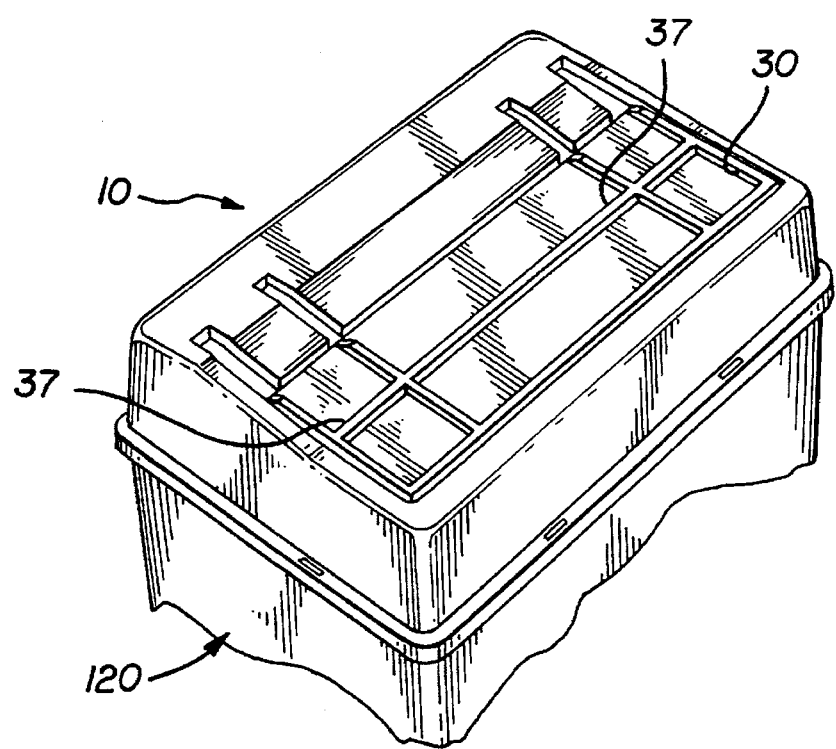
FIG. 2 is a perspective drawing of the top of the container showing the lid mount and the lid in its closed lid position.
Figure 3:
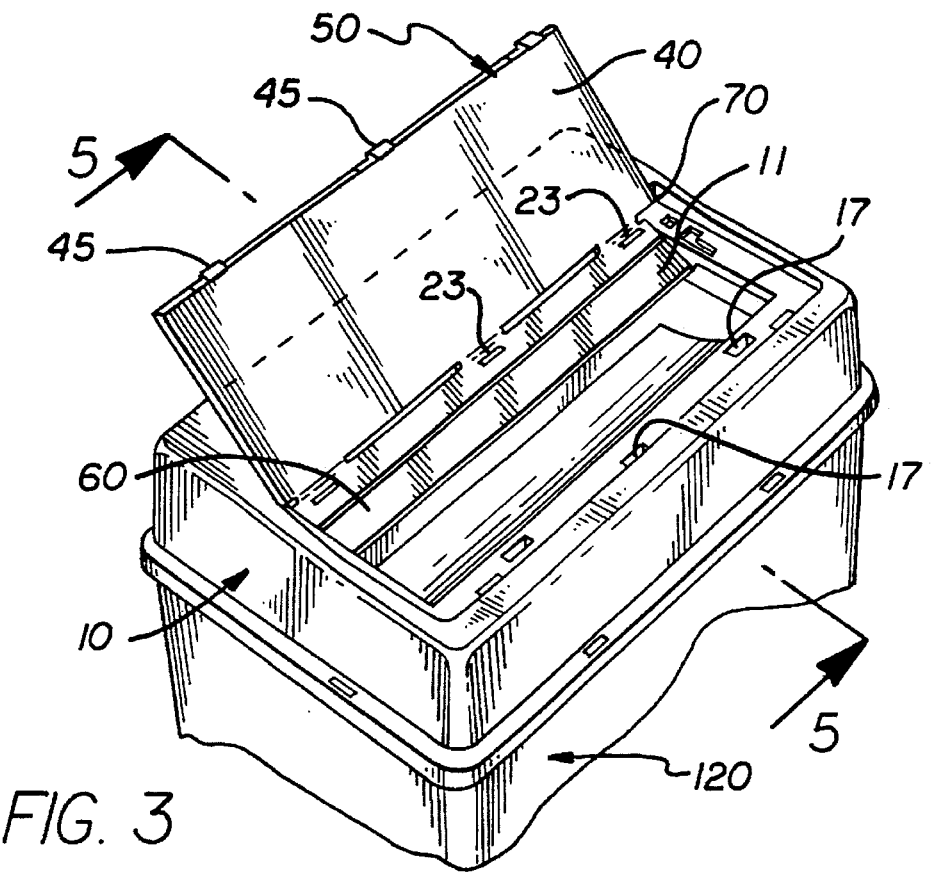
FIG. 3 is a perspective drawing showing the lid in an open position and the aperture in the lid mount through which waste articles may be deposited into the container.
Figure 4:
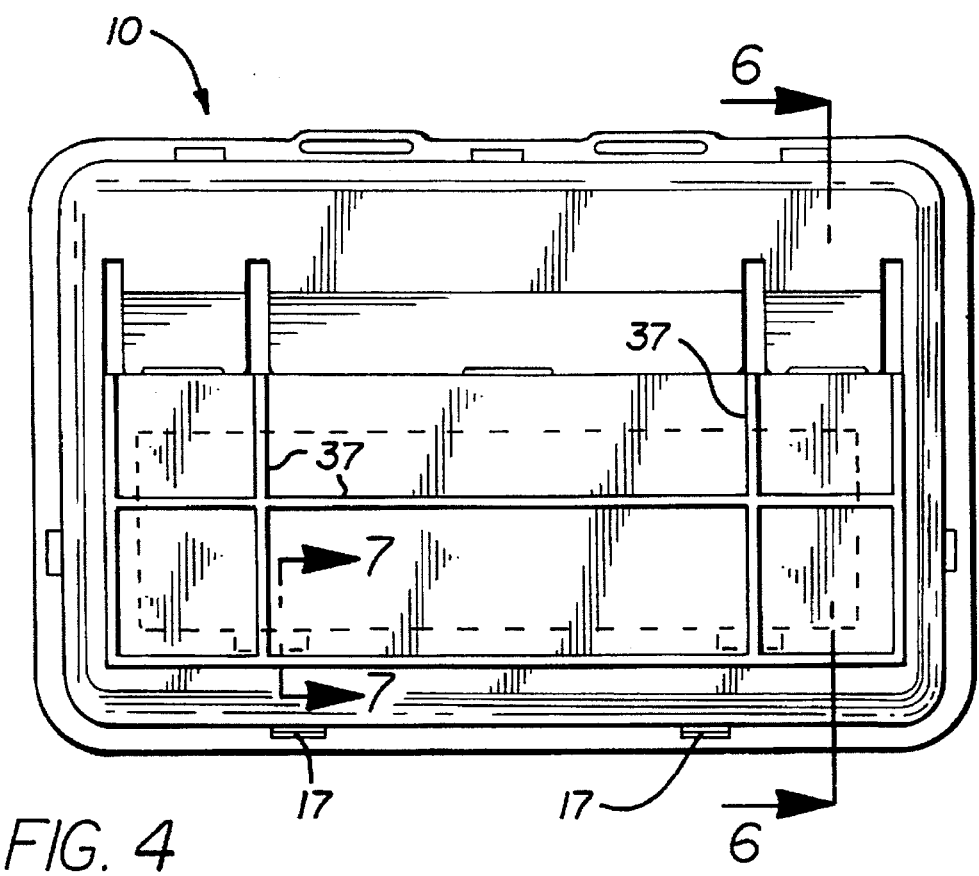
FIG. 4 is a vertical projection of the top plane of the lid mount showing the lid closed over the aperture, which it covers.
Figure 5:
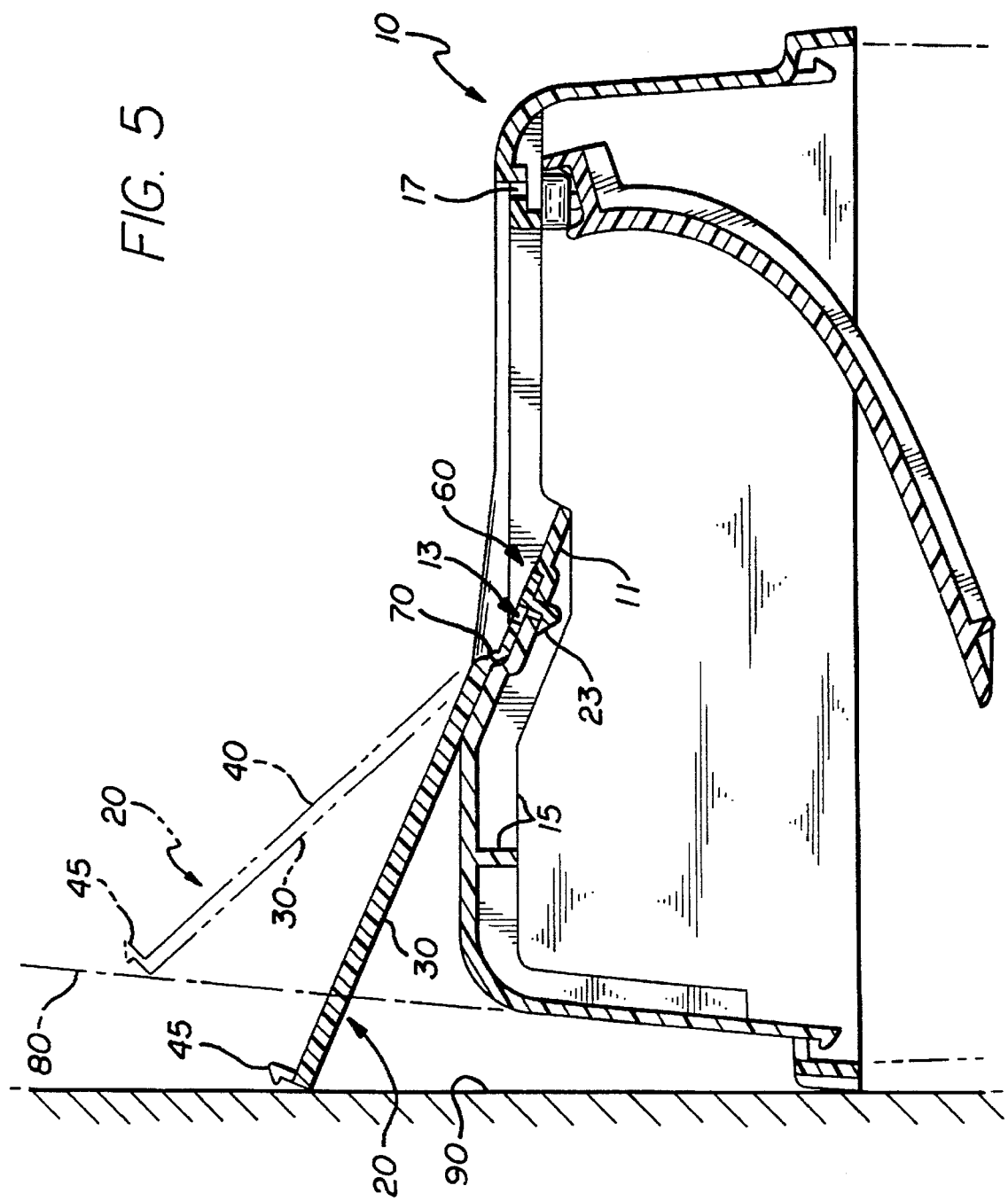
FIG. 5 is a cross-section in a vertical plane through the lines marked 5—5 in FIG. 3, showing the lid in an open position.
Figure 6:
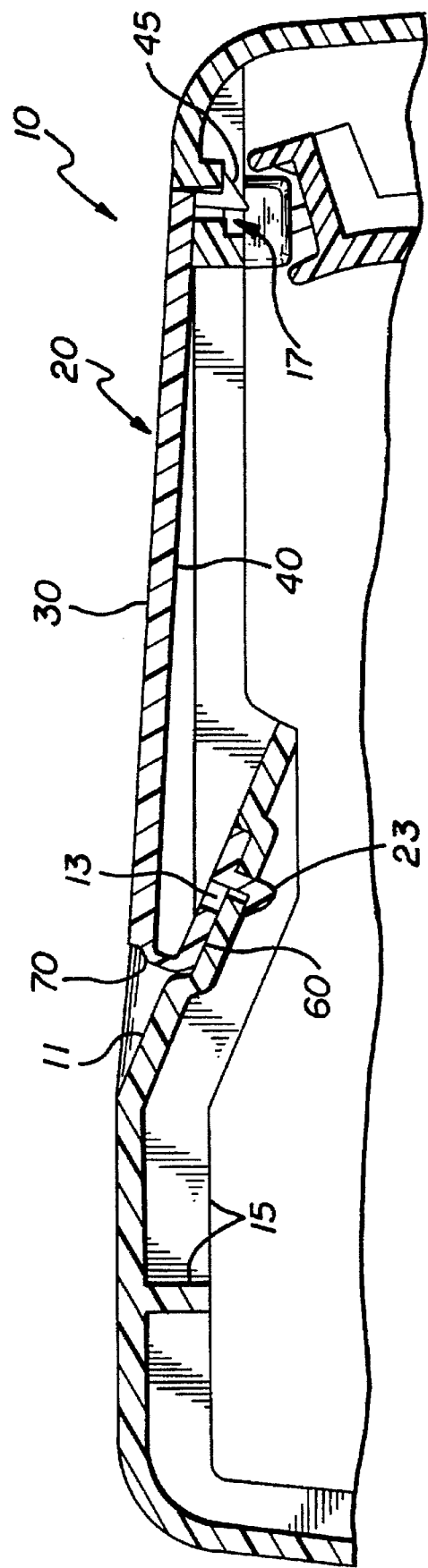
FIG. 6 is an enlargement of the upper half of FIG. 5 showing the lid in its closed and locked position.

As shown in FIGS. 1, 3, and 5 there is a flexible lid 20 which is hinged pivotally by living hinge 70 so that it can be left either in the open position shown in FIGS. 1, 3, and 5 or closed and locked over the aperture as in FIGS. 2, 4, and 6.

The free outer edge 50 of the unattached outer portion 30–40 of the lid 20, when the lid is unlocked, may move through the path 100 as shown in FIG. 1 when pressure is placed upon the lid 20, as by a mis-deposit of waste items intended for the entrance aperture but actually placed closer to the wall than the aperture. Note that when the lid 20 is flattened outwardly upon the recessed face 11 of the lid mount 10, the outer edge 50 of the lid 20 is so close to the wall 90 as to make it impossible to misplace an item intended for deposit, either between the container and the walls or behind the lid 20. In the preferred embodiment of the invention, the tension in the living hinge is so chosen that the natural equilibrium position is the maximally extended position just described. However, accidental mishandling of the lid by hospital personnel (who might decide tentatively to close and lock the lid, but then reverse the decision after having almost closed it) may alter the equilibrium position, as shown in the phantom structure drawings of FIG. 1 and, in greater detail, in FIG. 5, but this will not destroy the fail-safe utility of the present invention. Indeed, when the lid 20 is not maximally flattened outwardly, its damaged or unnatural equilibrium position may be in the partly opened position shown in FIGS. 1, 3, and 5, in which the inner face 40 of the outer portion of the lid 20 slopes toward the aperture; note that face 40 slopes continuously into the recessed face 11 of the lid mount 10, and together the face 40 and the recessed face 11 constitute a continuously sloping barrier between the wall and the hand of a person intending to deposit a waste item in the aperture. In the event of an accidental mis-deposition of waste upon the opened lid face 40, the waste item will be forced by gravity to roll or slide down the face 40 toward the face 11 and then fall into the aperture upon which the face 11 abuts. Accordingly this safety feature is operative whether or not the tension in the living hinge is as manufactured and first sold, or has been damaged by later mishandling.

Note as in FIG. 5 that the damaged or abnormal equilibrium position of the outer edge 50 of the lid 20 could be, for example, approximately in the same plane as the continuation 80 of the back face of the lid mount 10. This plane is not actually coincident with the plane of the wall 90 but it is sufficiently close that it is essentially impossible to place a waste item behind the lid 20 because pressure upon the lid 20 will flatten it into the normal or desired maximally extended position by motion such as shown by the dotted line 100 representing the path of such motion in FIG. 1; as mentioned, in this preferred flattened position, the outer edge 50 of the lid 20 is virtually in contact with the wall 90.

When in this maximally extended, flattened position, the outer face 30 of the outer portion of the lid 20 is parallel to the plane of the recessed face 11. Therefore the lid is never completely horizontal, even when maximally flattened, and so the gravitational safety feature of the lid 20 will be operational at all times.

The lid 20 is divided by the living hinge 70 into the outer portion 30–40 and an inner portion 60, which is permanently attached to the recessed face 11 by means of lid attachment hooks 23 which emerge from the underside of the inner portion 60 and fit into lid attachment slots 13 in the recessed face 11. The latch and slot arrangement attaches the inner portion 60 of the lid 20 permanently to the recessed face 11 of the lid mount 10.

The strength of the living hinge 70, which divides the inner and outer portions of the lid 20, is so chosen that the normal equilibrium position of the outer portion 30–40 of the lid 20 is somewhat above the recessed surface 11, as shown in FIGS. 1, 3, and 5.

The lid mount 10 may be strengthened by stiffening interior structural ribs 15, as shown in FIG. 5.

The lid 20 may also be locked in a closed position so as to seal the aperture, as shown in FIGS. 2, 4, and 6. In FIG. 2 the back face 30 of the lid 20 has now become the upper face when the lid 20 is in its closed and locked position.

The lid 20 may be strengthened by having stiffening structural ribs 37 on its outer portion as shown in FIGS. 2 and 4.

As shown in FIGS. 3, 5, and 6 there are lid latch hooks 45 disposed peripherally upon the outer portion of the lid 20, and there are corresponding latch slots 17 in the top face of the lid mount 10. The latch hooks 45 are sufficiently flexible that they may be forced through the latch slots 17, but after penetrating the slots 17 completely each of the hooks 45 springs into a natural equilibrium position, as shown in FIG. 6, which permanently locks the lid closed.

It should be noted that the lid mount 10 can be permanently attached to the container 120 by similar slot and hook arrangements, which are well known as standard elements of the prior art.

In the preferred embodiment just described, the stiffening structural ribs 15 and 37 are placed upon the outer surface 30 of the lid 20 (when the lid is in closed position), and in the interior of the lid mount 10; obviously these choices of interior and exterior locations of the ribs could be reversed without departing from the spirit of the present invention. Likewise the hooks and slots in the preferred embodiment are as depicted in FIGS. 1 through 6 but the hooks and slots could be changed from the lid mount to the lid and vice versa without departure from the invention taught here.

In addition to the embodiments described herein above, those skilled in the art will recognize that other embodiments are possible within the teachings of the invention. Accordingly the scope of the present invention should be limited only by the appended claims and their appropriately construed legal equivalents, rather than by the examples given.

What is claimed is:

1. A medical waste disposal device for use with a mounting device adapted to mount the medical waste disposal device on a wall, the medical waste disposal device comprising:

a container defining an open end;

a lid mount associated with the open end of the container, the lid mount defining a top portion, an entrance aperture and a sloping face arranged substantially adjacent to the entrance aperture; and a lid pivotally mounted on the sloping face of the lid mount and located such that a portion of the lid extends to the wall when the lid rests on the sloping face.

2. A wall mounted medical waste disposal device as claimed in claim 1, wherein the lid mount includes side portions integral with the top portion and the sloping face is recessed relative to the top portion.

3. A wall mounted medical waste disposal device as claimed in claim 1, wherein at least one of the container, lid mount and lid is composed of a preselected integrally molded material.

4. A wall mounted medical waste disposal device as claimed in claim 1, wherein the lid defines an axis of rotation extending in a predetermined direction and the sloping face includes stiffening structural ribs extending in substantially the same direction as the axis of rotation.

5. A wall mounted medical waste disposal device for use with a mounting device adapted to mount the medical waste disposal device on a wall, the medical waste disposal device comprising:

a container defining an open end;

a lid mount associated with the open end of the container, the lid mount defining a top portion, an entrance aperture and a sloping face arranged substantially adjacent to the entrance aperture; and a lid pivotally mounted on the lid mount and located such that a portion of the lid extends to the wall when the lid rests on the sloping face the lid including an inner portion and an outer portion pivotally attached to the inner portion, the inner portion being attached to the sloping face.

6. A wall mounted medical waste disposal device as claimed in claim 5, wherein the inner portion of the lid is arranged on the sloping face.

7. A wall mounted medical waste disposal device as claimed in claim 5, wherein a living hinge is arranged between the inner portion of the lid and the outer portion of the lid.

8. A wall mounted medical waste disposal device as claimed 7, wherein the living hinge is adapted to normally maintain the lid substantially against the sloping face.

9. A medical waste disposal device for use with a mounting device adapted to mount the medical waste disposal device on a wall, the medical waste disposal device comprising:

a container defining an open end;

a lid mount associated with the open end of the container, the lid mount defining a top portion, an entrance aperture and a sloping face adjacent to the entrance aperture; and a lid pivotally mounted on the sloping face of the lid mount and movable between a fully open position resting on a portion of the lid mount and a fully closed position over the entrance aperture, the lid being located on the lid mount such that a portion of the lid extends to the wall when the lid is in the fully open position and the disposal device is mounted on the wall by the mounting device.

10. A wall mounted medical waste disposal device as claimed in claim 9, wherein at least one of the container, lid mount and lid is composed of a preselected integrally molded material.

11. A wall mounted medical waste disposal device as claimed 9, wherein the lid comprises an inner portion and an outer portion pivotally attached to the inner portion, the inner portion being attached to the lid amount.

12. A wall mounted medical waste disposal device as claimed in claim 11, wherein a living hinge is arranged between the inner portion of the lid and the outer portion of the lid.

13. A wall mounted medical waste disposal device as claimed in claim 12, wherein the living hinge is adapted to normally maintain the lid substantially in the fully open position.

14. A wall mounted medical waste disposal device, comprising:

a container defining an open end;

a container mounting device adapted to mount the container on a wall;

a lid mount associated with the open end of the container, the lid mount defining a top portion, an entrance aperture and a sloping face arranged substantially adjacent to the entrance aperture; and a lid pivotally mounted on the lid mount, the lid including an inner portion and an outer portion pivotally attached to the inner portion, the inner portion being attached to the sloping face;

wherein the container, container mounting device, lid mount and lid are respectively dimensioned such that a portion of the lid extends to the wall when the lid rests on the sloping face.

15. A wall mounted medical waste disposal device as claimed in claim 14, wherein the inner portion of the lid is arranged on the sloping face.

16. A wall mounted medical waste disposal device as claimed in claim 14, wherein a living hinge is arranged between the inner portion of the lid and the outer portion of the lid.

17. A wall mounted medical waste disposal device as claimed in claim 16, wherein the living hinge is adapted to normally maintain the lid substantially against the sloping face.

\* \* \* \* \*